(12) United States Patent
Rolon et al.

(10) Patent No.: US 6,171,868 B1
(45) Date of Patent: Jan. 9, 2001

(54) METHOD OF SAMPLING BODILY FLUIDS

(75) Inventors: Noel Rolon, Belle Mead; William Pagels, Oceanport; Richard Egan, Flemington, all of NJ (US)

(73) Assignee: Ortho Pharmaceutical Corporation, Raritan, NJ (US)

( * ) Notice: Under 35 U.S.C. 154(b), the term of this patent shall be extended for 0 days.

(21) Appl. No.: 08/367,508

(22) Filed: Dec. 30, 1994

(51) Int. Cl.$^7$ .......................................... G01N 1/00
(52) U.S. Cl. ............................................... 436/174
(58) Field of Search ............................... 436/174

(56) References Cited

U.S. PATENT DOCUMENTS

| | | | |
|---|---|---|---|
| 4,277,249 | * 7/1981 | Broughton | 23/230 B |
| 5,204,267 | * 4/1993 | Sangha et al. | 436/14 |
| 5,413,761 | * 5/1995 | Dulaney | 422/56 |
| 5,427,953 | * 6/1995 | Yee | 436/74 |
| 5,432,092 | * 7/1995 | Yourno | 436/175 |

OTHER PUBLICATIONS

Tappin et al. "Prevalence of maternal HIV infection in Scotland based on unlinked anonymous testing of newborn babies" Lancet, 337, 1991, 1565–1567.*

Fortes et al Evaluation of Blood Collected on Filter Paper for Detection of Antibodies to Human Immunodeficiency Virus Type I–J of Clinical Microbiology, 6, 1989, 1380–1381, 27.*

Bell et al. Neonatal Thyroxine Screening by Use of a Single–Tube Solid–Phase Radioimmunoassay Clin. Chem, 24/10, 1978, 1755–58.*

Jinks et al. "Molecular genetic diagnosis of sickle cell disease using dried blood specimens on blotters used for newborn screening" Human Genetics 81, 1989, 363–366.*

Orfanos et al. "Fluorometric Micromethod for Determination of Arginase Activity in Dried Blood Spots" Clin. Chem, 26/8, 1980, 1198–1200.*

Standing et al. "Phenylalanine: application of a simple HPLC technique to its measurement in dried blood spots" Ann Clin Biochem. 1992, 29, 668–670.*

Mizejewski et al Commercial Radioimmunoassay Kit for Measurement of Alpha–Fetoprotein Adapted for Use w/ Dried Blood Specimens from Newborns, Clin. Chem. 28/5, 1207–1210, 1982.*

Konarska et al. ("A simple quantitative micromethod of arginase assay in blood spots dried on filter paper"). Clinica Chimica Acta, 154, 1986, 7–18.*

Ho et al. "Quantitative determination of porphyrins, their precursors, and zinc protoporphyrin in whole blood and dried blood by high–performance liquid chromatography with Fluorimetric detection" J. Chrom. 417 1987, 269–276.*

Sadler et al. "Blood–Spot Thyrotropin Radioimmunoassay in a Screening Program for Congenital Hypothyroidism"; Clin. Chem 25/6, 933–938, 1979.*

Varnier et al. "Whole Blood Collection on Filter Paper Is an Effective Means of Obtaining Samples for Human Immunodeficiency Virus Antibody Assay". Aids Research and Human Retroviruses, vol. 4, 2 1988, pp. 131–136.*

Maeda et al. "An Enzyme Linked Immunosorbent Assay for Thyroxine in Dried Blood Spotted on Filter Paper." J. Immunological Methods, 82, 1985, 83–89.*

* cited by examiner

*Primary Examiner*—Sharidan Carrillo
(74) *Attorney, Agent, or Firm*—Paul A. Coletti

(57) ABSTRACT

The invention provides for a method of making more than one punchout from a single dried blood spot. The method comprising the steps of making a first punch and sequentially making at least a second punch in the dried blood spot. The second punch comprises boundaries which are at least partly outside of the boundaries of the first punch. The surface areas of the first punch and second punch are together equivalent to the minimum surface area required for testing of the dried blood spot.

7 Claims, 2 Drawing Sheets

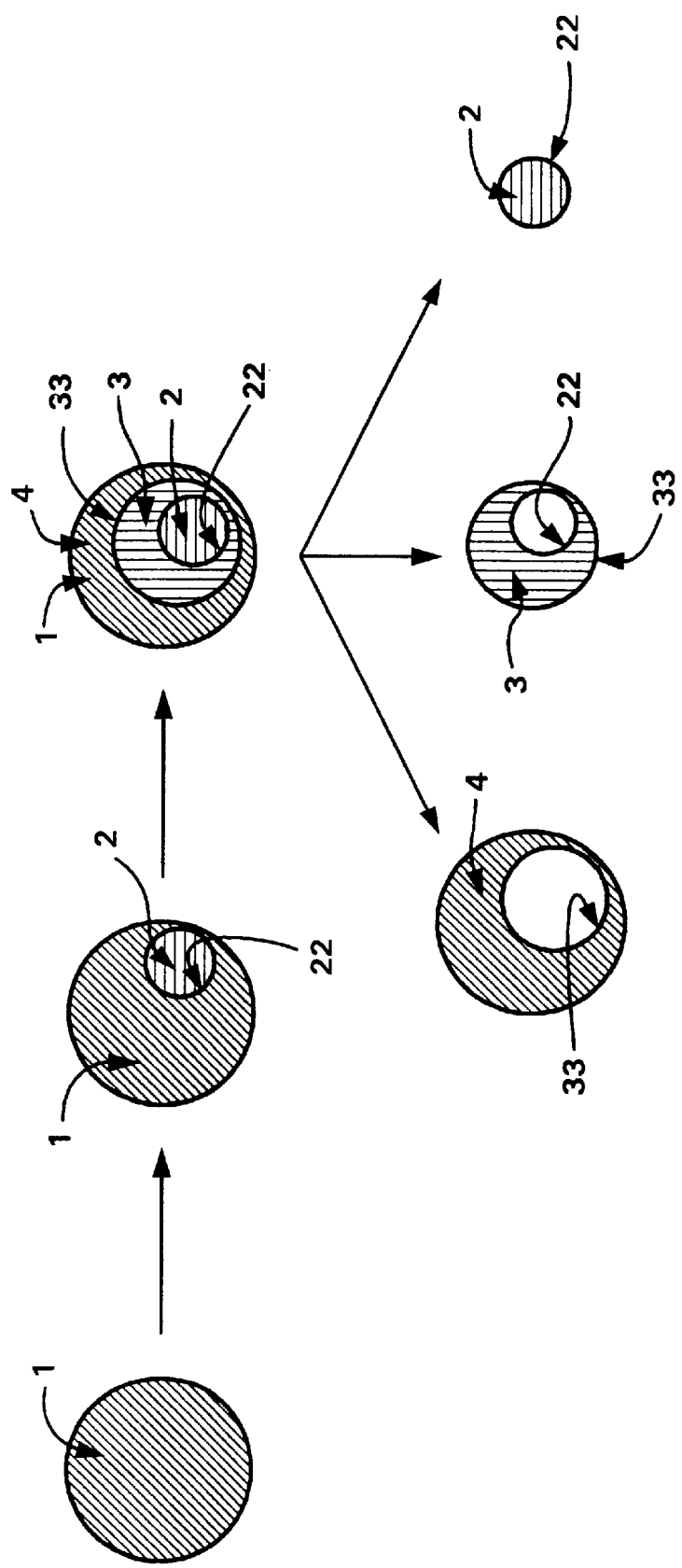

METHOD OF SAMPLING BODILY FLUIDS

BACKGROUND OF THE INVENTION

The ease with which small amounts of blood can be collected onto a filter paper and processed for testing has been of interest in utilizing dried-blood specimens in screening tests for blood-borne diseases such as acquired immunodeficiency syndrome. This technique provides distinct advantages over conventional techniques where access to refrigeration, centrifuges for blood separation, and large supplies of expensive disposal items are limited. Specimens of whole blood collected onto filter paper and dried are also easier and safer to ship than specimens collected by venipuncture.

Nationwide, human immunodeficiency virus type 1 (HIV-1) seroprevalence surveys using dried neonatal blood specimens are critical to estimating HIV-1 seroprevalence among childbearing women. However, the noninclusion of blood specimens deemed "quantity not sufficient" (QNS) for HIV-1 antibody testing potentially introduces bias. In HIV-1 seroprevalence surveys which utilize dried neonatal blood specimens, QNS rates can be reduced by the use of multiple ⅛ inch DBS to analyze specimens which are of insufficient quantity to test using a standard ¼ inch punch. By lowering QNS rates, the use of multiple ⅛ inch blood spots can be an effective way of assuring the accuracy of HIV-1 seroprevalence estimates. Redus et al. ("Use of the ⅛ inch Punch Method to Reduce QNS Rates and Improve Seroprevalence Estimates in the Survey in Childbearing Women", Centers for Disease Control and Prevention, Atlanta, Ga.), Hoxie et al. ("Improving Estimates of HIV-1 Seroprevalence Among Childbearing Women: Use of Smaller Blood Spots", *Am. J. Pub. Health,* October 1992, Vol. 82, No. 10, pgs 1370–1373) and Tappin et al. ("Prevalence of Maternal HIV Infection in Scotland on Unlinked Anonymous Testing of Newborn Babies", *The Lancet,* Vol. 337, Jun. 29, 1991, pgs 1565–1567) have described the use of DBS less than ¼ inch and the use of four ⅛ inch diameter punches in place of one ¼ inch diameter punch when one ¼ inch punch cannot be obtained.

The immunoassays designed to perform testing on patient samples are generally optimized for maximum detection of a minimal amount of a specific antibody in a given sample. Because of standard practice, these assays require a significant fraction, a ¼ inch or multiple ¼ inch punches of the DBS sample provided by a lay person. Therefore, more samples are required than can be provided by the standard-sized punch. Complete testing is not always possible using standard punch sizes. For example, enzyme immunoassays require elutions from separate DBS punches for testing and subsequent confirmatory assays require additional elutions from separate DBS punches.

The requirement of a ¼ inch punch is a limitation on the rate of compliance as most lay people are only able to provide a DBS which would yield a smaller size punch than the required ¼ inch punch. Moreover, because of the geometry of a circle, in order to obtain four ⅛ inch spots from one DBS, one would need at least one complete ½ inch DBS, or a mix of spots with varying diameters greater than ⅛ inch. In a clinical or hospital laboratory setting, this may be possible when obtaining samples from neonates. However, it is an impractical requirement from a lay person. Therefore, a method is required to punch a multitude of substandard size DBSs from the same DBS which would collectively be equivalent to the standard punch size required by a particular assay.

SUMMARY OF THE INVENTION

It is an object of this invention to provide for a method of obtaining more than one punch from a single dried blood spot.

It is another object of this invention to provide for a method of making a first punchout in a single dried blood spot and sequentially making at least a second punchout in the same dried blood spot with boundaries at least partly outside the boundaries of the first punchout.

It is yet another object of this invention to provide for a method of making at least a first and second punchout having together the minimum surface area required for testing of the dried blood spot.

These and other objects will be apparent from a reading of a remainder of this specification and claims.

DESCRIPTION OF THE FIGURES

FIG. 2 is a diagram of more than one eccentric punchout from one dried blood spot.

DESCRIPTION OF THE PREFERRED EMBODIMENTS

Figure 1:
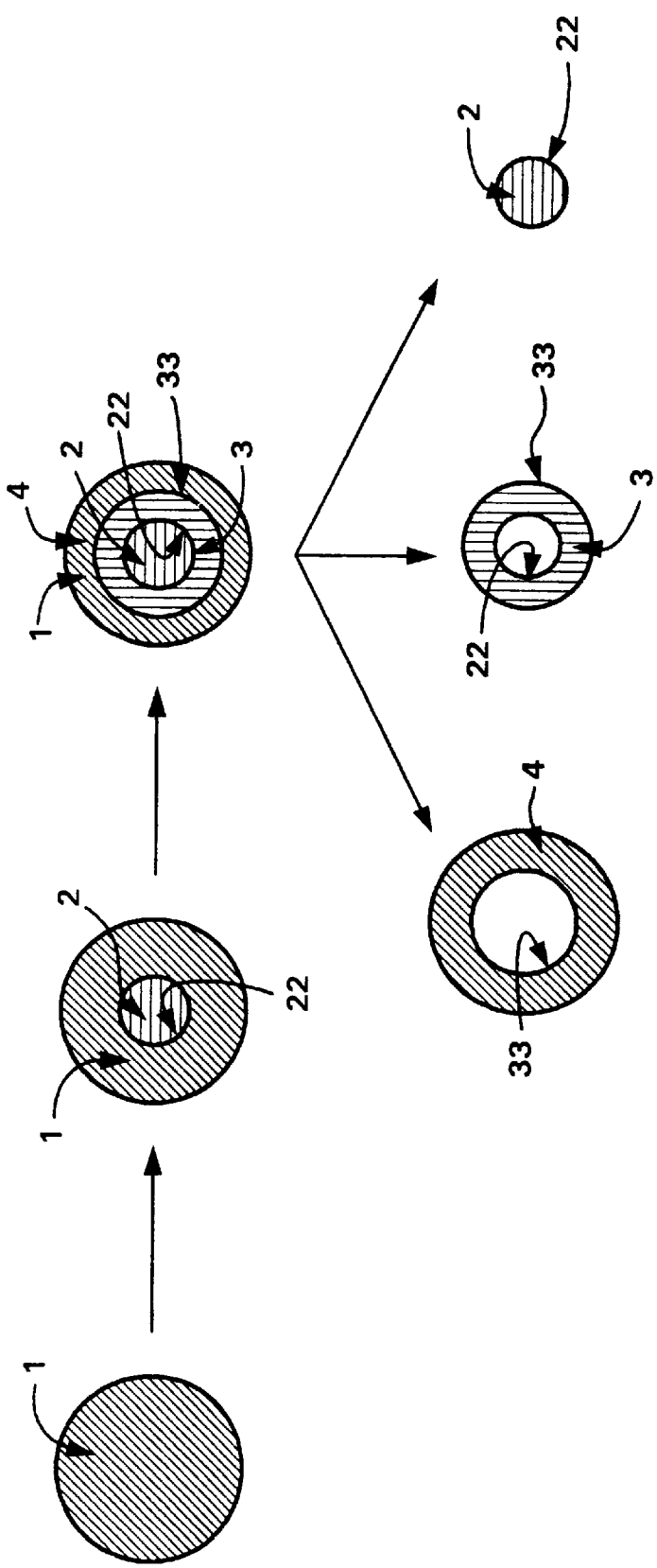
FIG. 1 is a diagram of more than one concentric punchout from one dried blood spot.

The invention provides for a method of obtaining more than one punch from a single bodily fluid spot. The method has applicability to any bodily fluid that can be spotted on the appropriate medium such as for example blood, urine, tears, saliva etc. The size and shape of the spot is limited by the medium on which the bodily fluid is absorbed, the punching means used to make the bodily fluid spot and by the assay that will be used to analyze for the spot.

More particularly, the invention finds applicability in the analysis of dried-blood specimens in screening tests for blood-borne diseases such as acquired immunodeficiency syndrome. Such specimens or dried blood spots are generally tested for HIV antibodies using any of the known assays including but not limited to any of the enzyme immunoassays, confirmatroy tests and amplification techniques using polymerase chain reaction.

The invention can also have applicability to the screening of phenylketonuria, metabolic disorders such as galactosemia, branched-chain ketonuria, hyperthyroidism, sickle-cell anemia, measles, rubella immunity testing, diabetes screening and monitoring blood lead levels.

For the testing of HIV antibodies, individuals can collect blood specimens by means of the Confide® card. The Confide® card is the subject matter of a copending patent application and consists of a test strip comprising a filter paper laminated between two layers of coated paperboard, with a window or cutout area exposing the front and back of the test strip. Three circles measuring about ⁵⁄₁₆ inch are printed on the front of the test strip window. Three circles measuring about ¼ inch are printed on the back, concentric within each front circle. The filter paper of the test strip conforms to the specifications set by the National Committee for Clinical Laboratory Standards. Card users can collect blood by applying a drop of blood to the filter paper portion. The drop of blood on the filter paper results in what is known as a dried blood spot (DBS).

Dried blood spots can also be obtained under simulated conditions using the Centers for Disease Control Procedure "Preparation of Dried Blood Spot Materials for Quality Assurance of Assays for Antibodies to Human Immunodeficiency Virus". Bench-level DBS quality control samples using HIV antibody-positive serum (or plasma) and antibody-negative serum combined with red blood cells to a hematocrit of 50±1%. Specific sample types are produced by using either negative serum and one donor positive serum or by blending two or more HIV-positive serum samples of different banding patterns. The DBS materials for performance evaluation (proficiency testing) are prepared in a similar manner by using one donor's serum with no blending or pooling of the serum. The whole blood materials are dispensed onto filter paper sheets to yield the appropriate enzyme immunosorbent assay (EIA) target absorbance values and Western Blot (WB) band and intensity patterns of high-positive, low-positive, and negative HIV antibody sample.

FIGS. 1 and 2 are an illustration of a particular embodiment of this invention. Starting with one dried blood spot 1, a first punchout 2 defined by outer boundaries 22 and a second punchout 3 defined by outer boundaries 33 and inner boundaries 22 can sequentially be made in dried blood spot 1. In this particular embodiment, punchout 2 can have a circular shape and punchout 3 can have a donut shape. A third punchout 4 having a donut and inner boundaries can also be obtained. FIG. 1 illustrates the particular embodiment wherein the punchouts are made in a concentric fashion. By contrast, FIG. 2 illustrates the particular embodiment wherein the punchouts are made in an eccentric fashion and as shown in FIG. 2, boundaries 22 and 33 can be tangential with punchouts 3 and 4 having a half-moon shape.

The total surface area of dried blood spot 1 and its diameter determine the amount of blood that is available for testing of HIV antibodies. For example, the diameter of dried blood spot 1 can be in the range of from about 1/16 and to about ½ inch and is generally limited by any of the tests described above. Conversely, the surface area of each punchout, is generally limited by the test that will be performed. In one application of the invention, when more than one punchout from the same dried blood spot are used for screening and confirmatory assays, the punchouts generally conform to the requirement of the minimum surface area required by the particular assay. For example, when an enzyme immunosorbent assay is used as a screening test, the minimum surface area can be about ⅛ to ¼ inch. Similarly, the same requirement can apply when immunofluorescence or Western Blot assays are used as confirmatory assays.

The invention and many of its attendant advantages will be understood from the foregoing description, and it will be apparent that various modifications and changes will be made without departing from the spirit and scope of the invention or sacrificing all of its material advantages, the specific materials, procedures and examples hereinbefore being merely preferred embodiments.

We claim:

1. A method of making more than one punchout from a single dried blood spot, the method comprising the steps of:
   making a first punchout in said dried blood spot, said first punchout having first boundaries; and
   sequentially making at least a second punchout in said dried blood spot, said second punchout having second boundaries, wherein said second boundaries are entirely outside of said first boundaries so that said second punchout has an inner portion removed therefrom, said inner portion forming said first punchout.

2. The method of claim 1 wherein the surface area of said first punchout and the surface area of said second punchout together are equivalent to the minimum surface area required for testing of said dried blood spot.

3. A method of making more than one punchout from a single dried blood spot, the method comprising the steps of:
   making a first punchout in said dried blood spot, said first punchout having a circular shape and having first boundaries; and
   sequentially making at least a second punchout in said dried blood spot, said second punchout having second boundaries, wherein said second boundaries are entirely outside of said first boundaries so that said second punchout has an inner portion removed therefrom, said inner portion forming said first punchout.

4. The method of claim 3 wherein the surface area of said first punchout and the surface area of said second punchout together are equivalent to the minimum surface area required for testing of said dried blood spot.

5. A method of making more than one punchout from a single dried blood spot, the method comprising the steps of:
   making a first punchout in said dried blood spot, said first punchout having first boundaries;
   sequentially making at least a second punchout in said dried blood spot, said second punchout having second boundaries, wherein said second boundaries are entirely outside of said first boundaries so that said second punchout has an inner portion removed therefrom, said inner portion forming said first punchout; and
   wherein the surface area of said first punchout and the surface area of said second punchout together are equivalent to the minimum surface area required for testing of said dried blood spot.

6. The method of claim 5 wherein said minimum surface area is that of an ¼ inch dried blood spot.

7. The method of claim 6 wherein the surface area of said first punchout is that of an ⅛ inch dried blood spot.

* * * * *